United States Patent [19]

Kaufman et al.

[11] Patent Number: 4,484,920

[45] Date of Patent: Nov. 27, 1984

[54] CONTAINER FOR MIXING A LIQUID AND A SOLID

[75] Inventors: Stephen B. Kaufman, Heather Ridge; John W. Hart, Winnetka; Richard Chamernik, Waukegan, all of Ill.

[73] Assignee: Baxter Travenol Laboratories, Inc., Deerfield, Ill.

[21] Appl. No.: 366,023

[22] Filed: Apr. 6, 1982

[51] Int. Cl.³ ........................ B65D 30/22; A61M 5/00

[52] U.S. Cl. .................................... 604/416; 604/410; 604/87

[58] Field of Search .............................. 604/56, 82–89, 604/91, 92, 262, 403, 408–410, 416; 206/219, 222

[56] References Cited

U.S. PATENT DOCUMENTS

| | | | |
|---|---|---|---|
| 2,735,430 | 2/1956 | Huber . | |
| 2,798,488 | 7/1957 | Hall | 604/82 |
| 2,800,269 | 7/1957 | Smith . | |
| 2,904,043 | 9/1959 | Friedman . | |
| 2,955,595 | 10/1960 | Semple . | |
| 3,001,525 | 9/1961 | Hendricks | 604/416 |
| 3,033,202 | 5/1962 | Richter et al. . | |
| 3,033,203 | 5/1962 | Barton . | |
| 3,059,643 | 10/1962 | Barton . | |
| 3,110,309 | 11/1963 | Higgins . | |
| 3,123,072 | 3/1964 | Bellamy, Jr. . | |
| 3,150,661 | 9/1964 | Maki . | |
| 3,214,504 | 10/1965 | Gemberling . | |
| 3,260,777 | 7/1966 | Brandt . | |
| 3,286,010 | 11/1966 | Van Groningen . | |
| 3,336,924 | 8/1967 | Sarnoff et al. . | |
| 3,369,708 | 2/1968 | Hein . | |
| 3,375,824 | 4/1968 | Krakauer et al. . | |
| 3,470,867 | 10/1969 | Goldsmith . | |
| 3,477,432 | 11/1969 | Shaw . | |
| 3,542,023 | 11/1970 | Ogle . | |
| 3,548,825 | 12/1970 | Shaw . | |
| 3,578,037 | 5/1971 | Flynn . | |
| 3,608,709 | 9/1971 | Pike . | |
| 3,659,602 | 5/1972 | Cloyd . | |
| 3,662,930 | 5/1972 | Meierhoefer . | |
| 3,776,996 | 12/1973 | Cameron et al. . | |
| 3,783,997 | 1/1974 | Brown . | |
| 3,788,369 | 1/1974 | Killinger . | |
| 3,826,260 | 7/1974 | Killinger . | |
| 3,826,261 | 7/1974 | Killinger . | |
| 3,828,779 | 8/1974 | Ogle . | |
| 3,841,329 | 10/1974 | Killinger . | |
| 3,872,867 | 3/1975 | Killinger . | |
| 3,908,654 | 9/1975 | Lhoest et al. . | |
| 3,976,073 | 8/1976 | Quick et al. . | |
| 3,985,135 | 10/1976 | Carpenter | 604/410 |
| 4,021,524 | 5/1977 | Grimsley . | |
| 4,157,723 | 6/1979 | Granzow et al. . | |
| 4,181,140 | 1/1980 | Bayham et al. . | |
| 4,223,675 | 9/1980 | Williams . | |
| 4,259,952 | 4/1981 | Avoy | 604/56 |
| 4,265,280 | 5/1981 | Ammann et al. . | |
| 4,282,863 | 8/1981 | Beigler . | |
| 4,294,247 | 10/1981 | Carter et al. . | |
| 4,325,417 | 4/1982 | Boggs et al. . | |
| 4,340,049 | 7/1982 | Munsch . | |
| 4,392,851 | 7/1983 | Elias | 604/416 X |
| 4,411,662 | 10/1983 | Pearson . | |
| 4,434,822 | 3/1984 | Bellamy . | |
| 4,465,488 | 8/1984 | Richmond . | |

FOREIGN PATENT DOCUMENTS

| | | |
|---|---|---|
| 1373027 | 8/1964 | France . |
| 2473017 | 7/1981 | France . |
| WO81/01241 | 5/1981 | PCT Int'l Appl. . |
| 1591989 | 7/1981 | United Kingdom . |

OTHER PUBLICATIONS

Photocopy of NUTRIFLEX® Container sold by Vifor, S.A., Geneva, Switzerland.

*Primary Examiner*—C. Fred Rosenbaum
*Assistant Examiner*—Michelle N. Lester
*Attorney, Agent, or Firm*—John P. Kirby, Jr.; Garrettson Ellis; Bradford R. L. Price

[57] ABSTRACT

A container adapted for the mixing of a liquid and a solid initially placed in separate compartments. The compartment containing the solid has two access ports so liquid can pass through the compartment carrying the solid with it for better mixing.

1 Claim, 3 Drawing Figures

CONTAINER FOR MIXING A LIQUID AND A SOLID

TECHNICAL FIELD AND PRIOR ART

Many medicines such as antibiotics are desirably stored in a dry powder form, but prior to intravenous administration to a patient they must be reconstituted into a solution with a sterile water, saline, or dextrose solution without contamination of the mixture.

In Bellamy et al. U.S. patent application Ser. No. 315,399, filed Oct. 27, 1981 and entitled "SYSTEM FOR THE STERILE MIXING OF MATERIALS", a system for the sterile connection between a vial containing a solid material and a flexible liquid container is disclosed, in which the vial typically carries an access port which is brought into flow communication with the solution container. The solution then is driven into the vial to disperse and dissolve the solid contents thereof, and then drawn back into the solution bag for administration to the patient.

Also, Travenol Laboratories, Inc. of Deerfield, Illinois sells its MINIBAG ® container for the purpose of connection with vials of lyophilized drugs, to reconstitute them into solutions.

However, in some circumstances difficulties can arise in the dispersion or dissolution of the solid material in the liquid. If the vial containing the solid is small and rigid, as is quite common, it may be difficult to insert a large amount of liquid into the vial, with the result that it becomes necessary to go through a considerable number of manipulations to get the solid contents of the vial well dispersed or dissolved into the liquid. One may have to shake the system for a considerable period of time, and also to go through several cycles of inserting and draining liquid to and from the rigid vial.

In accordance with this invention, an improved system for the mixing of a liquid and solid which are initially placed in separate compartments is provided. Furthermore, the system may be an integral system, not utilizing separate containers which are brought together by the user, but integral from the beginning. However, if desired, this invention may also be used with separate solution and solid containers.

In this invention, the solution can pass through the solid-containing compartment into a third compartment, so that a greatly increased flow of solution can pass through the solid containing compartment. As the result of this, the solid material initially contained in the solid-containing compartment can be more easily dispersed or dissolved.

DESCRIPTION OF THE INVENTION

In accordance with this invention, a container is adapted for the mixing of a liquid and a solid initially placed in separate compartments, without opening the container to the exterior. The container of this invention comprises a first, liquid-containing compartment and a second, solid-containing compartment. A first, sealed port having first seal means openable from outside of the container permits flow communication between the first and second compartments when opened. A third compartment is also provided, as well as a second port permitting flow communication between the second and third compartments.

When both the first and second ports are opened, liquid can be forced through the first port into the solid-containing compartment, from where it passes through the second port into the third compartment. Accordingly, a perceptible current of flowing solution can pass through the solid-containing compartment, dispersing and dissolving with greater efficiency the solid contents, even when the solid contents constitute a drug or other material which dissolves or disperses only with difficulty.

The first compartment is preferably flexible and collapsible, being typically part of a collapsible solution container which may, except for the modifications of this invention, be of ordinary design.

The second port preferably carries a second seal which is openable from the outside of the container to permit flow communication after opening between the second and third compartments when open, and the third compartment typically also carries at least enough liquid to prevent adhesion of its walls during heat sterilization, when such is used. Otherwise, the third compartment may be initially empty.

As stated above, the liquid may be any desired diluent, but typically in the medical field is sterile water or normal saline or dextrose solution. The solid in the solid-containing compartment may be any appropriate drug or other material, for example an antibiotic such as Gentamicin sulphate or Cefazolin sodium. Similarly, other drugs such as Cimetidine or cancer therapeutic agents such as 5-fluorouracil may be utilized in the system of this invention. The use of this invention is also not limited to the pharmaceutical field, but may be used in any situation where it is desired to store solid or other material apart from a diluent liquid, and then to mix the material into the liquid, preferably without opening of the outer container.

The container of this invention may be sterilized as desired, for example by modification in accordance with the teachings of the application of William Schnell, filed concurrently herewith and entitled "STERILIZED LIQUID MIXING SYSTEM" U.S. patent application Ser. No. 365,940.

Description of Specific Embodiment

Figure 1:
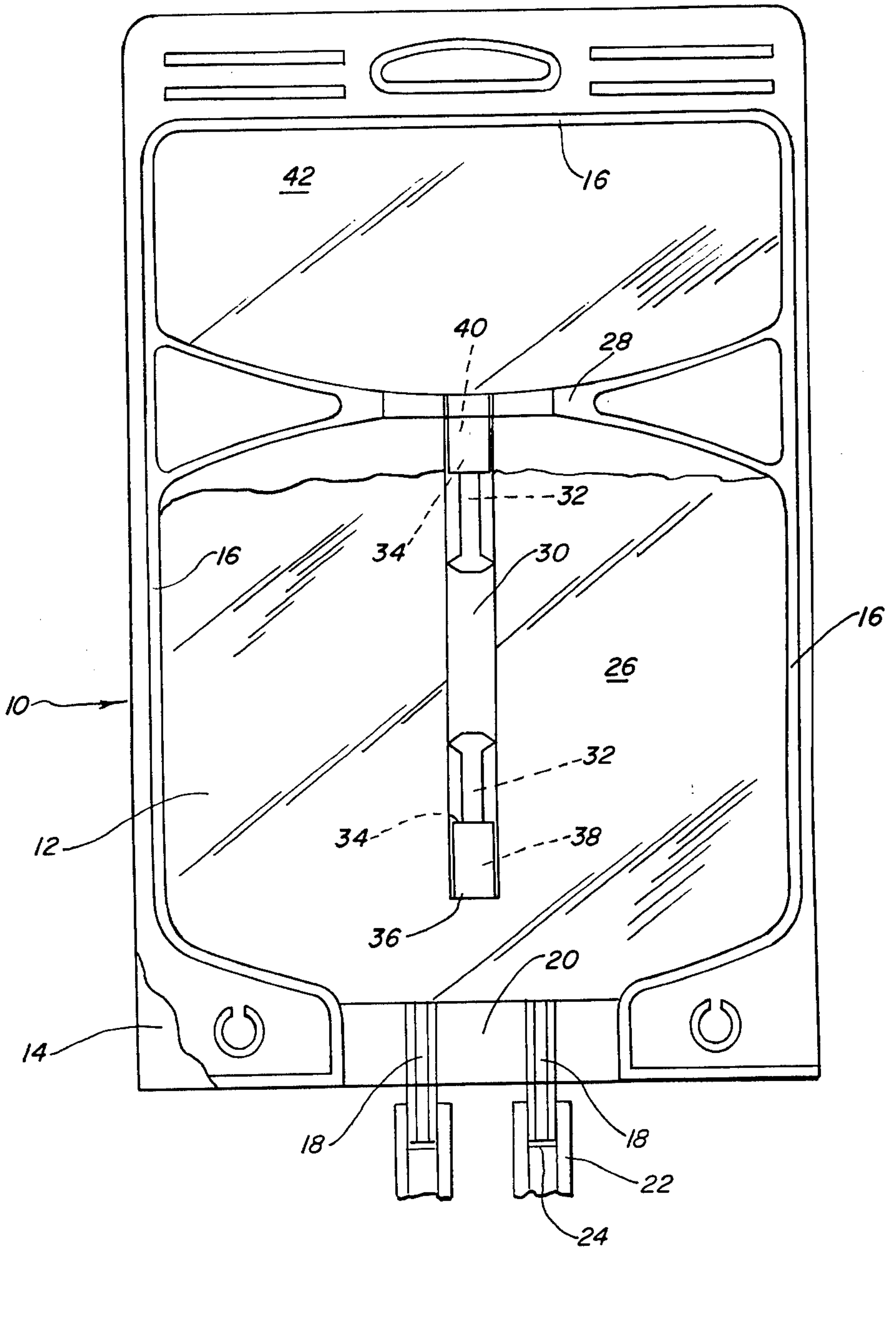
FIG. 1 is a plan view of one embodiment of the invention of this application, with a portion broken away.

Referring to FIG. 1, a first embodiment of the container of this invention is disclosed. Container 10 comprises a pair of heat sealed plastic sheets 12, 14 which may be made of polyvinyl chloride plastic or any other desired thermoplastic material. Alternatively, container 10 may be a blow molded, collapsible container if desired, or any other suitable design. In the particular embodiment shown, plastic sheets 12, 14 are sealed together about a peripheral seal line 16 in generally conventional manner. A pair of access ports 18 are provided, extending through sealed area 20 to provide access to the container and containing an outer, telescopically-carried access tube 22 which, in turn, carries a frangible membrane 24 in accordance with conventional technology.

In accordance with this invention, container 10 defines a first, liquid-containing compartment 26, being defined heat seals 16, 20 and further defined at its upper end by transverse heat seals 28 between sheets 12 and 14. Tube 30, made of flexible plastic, may be carried within heat seal 28 for retention thereof, being positioned within bag 10 and in the specific embodiment shown primarily occupying first compartment 26. Flexible tube 30 is shown to be sealed at both ends by means of a frangible breakaway seal 32 which may be broken off to open each end of tube 30 by appropriate bending of tube 30, to rupture frangible seal 32 at annular line of weakness 34.

Breakaway members 32 may, for example, be of a design as disclosed in U.S. Pat. Nos. 4,181,140 or 4,294,247, or U.S. Pat. application Ser. No. 86,102, filed Oct. 18, 1979 now U.S. Pat. No. 4,340,049.

Furthermore, if desired, while breakaway members 32 are shown to be projecting inwardly of tube 30 in FIG. 1, they may alternatively project outwardly from tube 30 so that the projecting members 32 which break away are not within tube 30 at all, but when they break away simply fall into the respective chambers of bag 10.

As a further alternative, hollow needles or spikes may be used to penetrate a diaphragm at the opposed ends of tube 30 as an alternative technique for opening tube 30. In this instance, tube 30 may be rigid, for example, made of glass or other material having a low vapor transmission rate, with the cannulas or needles being positioned so that they can be pushed through the diaphragm by manipulation from outside the bag so that access to tube 30 from both ends can be obtained without opening of the bag.

Tube 30 communicates at its lower end 36, through tubular mount 38 that carries breakaway member 32, with first liquid-containing compartment 26. The interior of tube 30 may contain the desired solid material such as an antibiotic or the like for mixing with the liquid. Thus, upon opening of the breakaway members 32, liquid from compartment 26 can pass into tube 30 to disperse and dissolve the solid contents of the tube.

Upper tubular mount 40 carries the upper frangible member 32 so that when it is opened, a second port is provided permitting flow communication between the interior of tube 30 and third compartment 42, which typically is partially filled with liquid, but in the alternative may be empty. Because of the presence of third compartment 42, after opening of seals 32 it becomes an easy matter to simply squeeze bag 10 to force liquid from compartment 26 through tube 30 with abundant flow into third compartment 42, carrying the solid contents of tube 30 therewith for dispersion and dissolution. The liquid may then be transferred back from third compartment 42 into first compartment 26 through tube 30, with this process being easily repeated until the solid contents of the system are completely dispersed or dissolved.

Thereafter the dissolved liquid contents may be administered from first compartment 26 by a conventional spike connection through one of the access ports 18.

Figure 3:
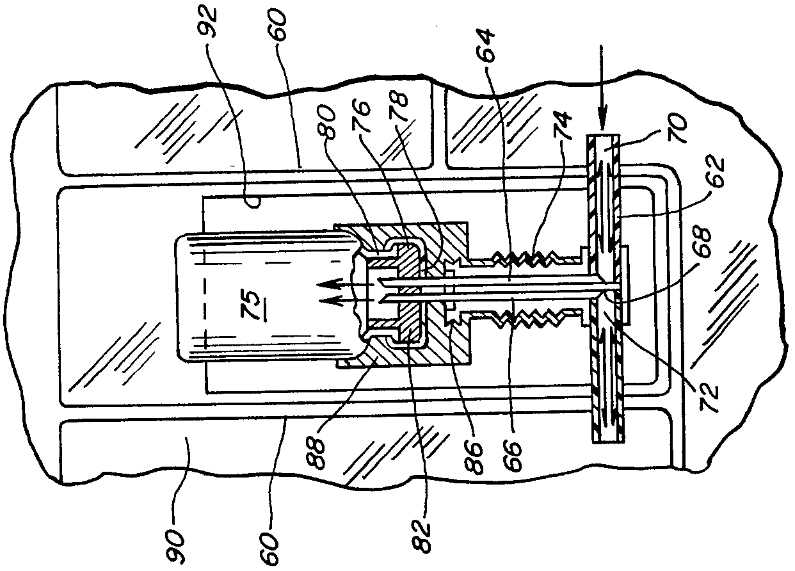
FIG. 3 is an enlarged fragmentary plan view of the container of FIG. 2, taken partly in longitudinal section, and showing the container in its open configuration in which there is flow communication between the liquid-containing and solid-containing compartments.
Figure 2:
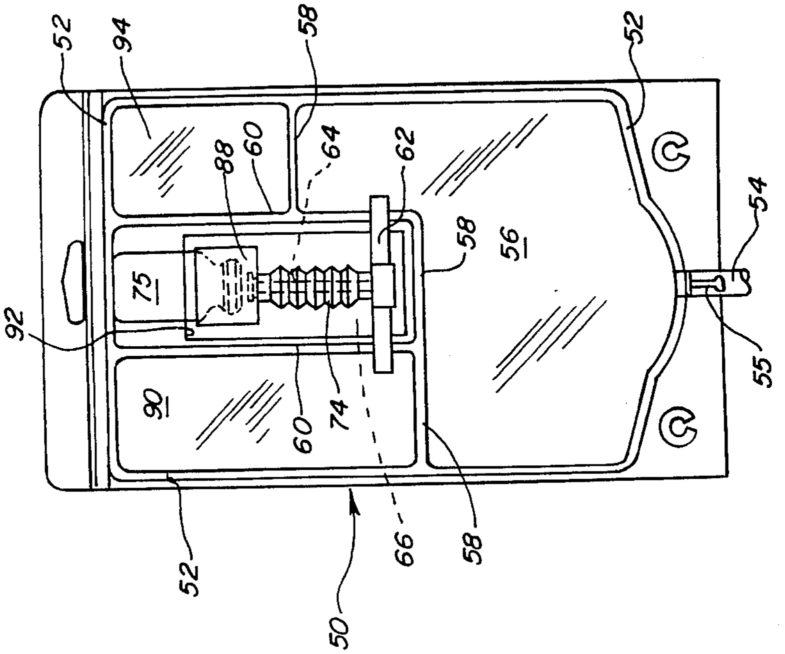
FIG. 2 is a plan view of another embodiment of the invention of this application, shown in its initial configuration when the liquid and solid-containing compartments are sealed.

Referring now to the embodiment of FIGS. 2 and 3, another embodiment of the container of this invention is disclosed.

Container 50 may be a sealed envelope as in the previous embodiment, formed from a pair of plastic sheets by a peripheral seal line 52 in accordance with generally conventional technology. Entry port 54 passes through seal line 52 into a first chamber 56 which is defined within envelope or bag 50 by a portion of seal line 52, and also inner seal lines 58, to fully define chamber 56 in sealed manner. A breakaway seal member 55 may be provided, of a design similar to member 32.

Added seal lines 60 are formed in bag 50 and carry tubular conduit 62 sealed adjacent its respective ends in each of the seal lines 60.

Projecting from tubular conduit 62 is a pair of hollow penetrating needles 64, 66 separated by flow blocking partition 68 in conduit 62 so that conduit 62 defines a pair of separate flow channels 70, 72 that respectively communicate with needles 64, 66. Flexible boot 74 is provided, being carried by conduit 62 and surrounding hollow needles 64, 66.

As shown in FIG. 3, a vial 75 or other container serves as the second compartment. Vial 75 in itself may be of the conventional construction of a drug vial, defines a cap seal 76 about its neck 80 having an aperture 78 at its outer end to surround and retain a latex needle-puncturable seal member 82, which may be of generally conventional design. Second compartment 75 may be connected to an end flange 86 of flexible boot 74 by a molded mass of preferably thermoplastic material 88, which is molded about flange 86 and neck 80 of container 75, to firmly retain the two members together.

In the initial configuration of FIG. 2, needles 64, 66 are preferably wholly positioned within boot 74, but boot 74 is longitudinally collapsible, permitting needles 64, 66 to penetrate outwardly through an aperture in flange 86, through the thermoplastic mass 88, aperture 78, and latex needle-penetrable seal, for access to the interior of container or vial 75. The formation and use of plastic mass 88 to retain vial 75 in connection with flange 86 is as disclosed in the concurrently filed U.S. application of Stephen Pearson entitled "STERILE COUPLING" U.S. patent application Ser. No. 365,943, now U.S. Pat. No. 4,411,662.

Flow channel 72 of conduit 62 communicates at one end with hollow needle 66 and at its other end with a third chamber 90, defined in bag 50 by appropriate seal lines 52, 58, and 60.

An aperture 92 may be cut in one or both of the two plastic sheets of bag 50 for purposes of convenient manufacture. Bag 50 may be formed, and then vial 74 may be separately molded in place with respect to flange 86.

Space 94 in bag 50 may be an unused area, or it may be part of first chamber 56 by the elimination of seal line 58, or it may be used as a holding pouch.

In use, chamber 56 may be filled with liquid diluent. When it is desired to mix the typically solid contents of vial 75 with the liquid diluent of chamber 56, vial 75 is manually advanced against needles 64, 66, with boot 74 collapsing longitudinally in the process, so that the structure goes from the configuration of FIG. 2 to that of FIG. 3, where the pair of needles 64, 66 penetrate latex seal 82 for access to the interior of vial 75. The walls of chamber 56 can then be squeezed, causing liquid to run through flow path 70 and needle 64 into vial 75, with air venting through needle 66 and flow path 72 into third chamber 90. Liquid pouring into vial 75 in this manner can also flow out in the same flow path through needle 66 and flow path 72 into third chamber 90, causing a flushing action for facilitated and rapid dissolution or dispersion of the contents of vial 75.

When chamber 90 is filled, it can be squeezed, causing a reverse flushing flow in the other direction, with the result that, after some simple manipulation, the thoroughly mixed materials may be replaced back into first chamber 56, ready for administration through port 54 upon the breaking of internal seal member 55.

The above has been offered for illustrative purposes only, and is not intended to limit the scope of the invention of this application, which is as defined in the claims below.

That which is claimed is:

1. A container adapted for the mixing of a liquid and a solid initially placed in separate compartments, without opening the container to be exterior, said container comprising:

a flat-collapsible container defining a pair of walls sealed together by seal lines, some of said seal lines passing transversely across said container to define a pair of compartments, a tube communicating between said pair of compartments through said seal line, said tube being sealed at both end with seal means openable from outside of said container to permit flow communication between said compartments through said tube when opened, said tube containing said solid and one compartment containing said liquid, the other of said compartments being one of (a) empty and (b) partially filled with liquid.

* * * * *

UNITED STATES PATENT AND TRADEMARK OFFICE

CERTIFICATE OF CORRECTION

PATENT NO. : 4,484,920

DATED : November 27, 1984

INVENTOR(S) : Stephen P. Kaufman, et al.

It is certified that error appears in the above-identified patent and that said Letters Patent are hereby corrected as shown below:

In Claim 1, column 6, line 1, change "be" to --the--.

In Claim 1, column 6, line 8, change "end" to --ends--.

Signed and Sealed this

*Ninth* Day of *April 1985*

[SEAL]

*Attest:*

DONALD J. QUIGG

*Attesting Officer*

*Acting Commissioner of Patents and Trademarks*